US00PP35693P2

(12) United States Plant Patent
Bean et al.

(10) Patent No.: US PP35,693 P2
(45) Date of Patent: Mar. 12, 2024

(54) ***GAZANIA* PLANT NAMED 'DWGZHY01'**

(50) Latin Name: ***Gazania krebsiana* x *Gazania rigens***
Varietal Denomination: DwGzHy01

(71) Applicant: De Wet Plant Breeders, Johannesburg (ZA)

(72) Inventors: Quinton Bean, Northriding (ZA); Charles Andrew De Wet, Sandton (ZA)

(73) Assignee: DE WET PLANT BREEDERS, Johannesburg (ZA)

( * ) Notice: Subject to any disclaimer, the term of this patent is extended or adjusted under 35 U.S.C. 154(b) by 0 days.

(21) Appl. No.: 18/124,567

(22) Filed: Mar. 21, 2023

(30) Foreign Application Priority Data

Dec. 14, 2022 (QZ) ..... PBR 20222939

(51) Int. Cl.
*A01H 5/02* (2018.01)
*A01H 6/14* (2018.01)

(52) U.S. Cl.
USPC ..... Plt./334

(58) Field of Classification Search
USPC ..... Plt./263.1, 334
See application file for complete search history.

*Primary Examiner* — Karen M Redden
(74) *Attorney, Agent, or Firm* — Penny J. Aguirre

(57) ABSTRACT

A new cultivar of *Gazania* plant of hybrid origin named 'DwGzHy01' that is characterized by its large inflorescences, its bi-colored ray florets that are yellow and orange in color, its floriferous blooming habit, its non-spreading plant habit and lacks production of viable seeds, its good disease resistance to *Fusarium* spp., its clean green foliage, its low growing habit and suitability for use as a groundcover, its high heat and drought resistance, and its vigorous growth habit.

3 Drawing Sheets

Botanical classification: *Gazania krebsiana* x *Gazania rigens*.

Variety denomination: 'DwGzHy01'.

CROSS REFERENCE TO RELATED APPLICATIONS

This application claims priority to European Community Plant Variety Office (CPVO) Plant Breeder's Rights Application No. 2022/2939 filed Dec. 14, 2022. The Applicant received the information for the Plant breeders' rights application directly from the Inventors.

BACKGROUND OF THE INVENTION

The present invention relates to a new and distinct cultivar of *Gazania* plant, botanically of interspecific hybrid origin and known as *Gazania* 'DwGzHy01' and will be referred to hereinafter by its cultivar name, 'DwGzHy01'. The new cultivar of *Gazania* is an herbaceous perennial plant grown for landscape and container use.

The new cultivar was derived from a controlled breeding program by the Inventors in Hartebeespoort, North West Province, South Africa. The goal of the breeding program was to develop a new cultivar of *Gazania* with neat foliage, bi-colored flowers, a strong, vigorous, and floriferous plant habit, resistance to heat and disease that is non-spreading and lacking viable seed production. The Inventors made a cross in 2017 between an unpatented and unnamed proprietary plant of *Gazania krebsiana* from the Inventors' breeding program as the female and an unpatented and unnamed proprietary plant of *Gazania rigens* from the Inventors' breeding program as the male parent. The Inventors selected 'DwGzHy01' in 2018 as a single unique plant amongst the seedlings that resulted from the above cross.

Asexual propagation of the new cultivar was first accomplished by division under the direction of the Inventors in Hartebeespoort, North West Province, South Africa in 2018. Asexual propagation by division and tissue culture using meristematic tissue has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'DwGzHy01' as a unique cultivar of *Gazania*.

1. 'DwGzHy01' exhibits large inflorescences.
2. 'DwGzHy01' exhibits bi-colored ray florets that are yellow and orange in color.
3. 'DwGzHy01' exhibits a floriferous blooming habit.
4. 'DwGzHy01' exhibits a non-spreading plant habit with lack of viable seeds production.
5. 'DwGzHy01' exhibits good disease resistance to *Fusarium* spp.
6. 'DwGzHy01' exhibits clean green foliage.
7. 'DwGzHy01' exhibits blooms that are self-cleaning.
8. 'DwGzHy01' exhibits a low growing habit and suitability for use as a groundcover.
9. 'DwGzHy01' exhibits high heat and drought resistance.
10. 'DwGzHy01' exhibits a vigorous growth habit.

The female parent of 'DwGzHy01' differs from 'DwGzHy01' in having a smaller plant size and a less vigorous plant habit. The male parent of 'DwGzHy01' differs from 'DwGzHy01' in having flowers with ray florets that are solid yellow in color (not bi-colored). 'DwGzHy01' can be most closely compared to *Gazania rigens* cultivar NEW DAY 'Yellow' (not patented) and *Gazania* 'Moonglow' (not patented). NEW DAY 'Yellow' differs from 'DwGzHy01' in having inflorescences with ray florets that are yellow with small brown-black markings in the centers, less resistance to *Fusarium* spp. and heat resistance, and production of viable seeds. 'Moonglow' differs from 'DwGzHy01' in having a low resistance to *Fusarium* spp., flowers that are smaller in size, ray florets that are solid yellow in color and a creeping-spreading plant habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Thompson & Morgan, Dobies, Visions Pictures, Linkdin, Instagram, Facebook, Vanmeuwen, Suttons, BHG, CND Nursery, Anglian gardner, and Friedrichstrauss.

BRIEF DESCRIPTION OF THE DRAWINGS

The accompanying color photographs illustrate the overall appearance and distinct characteristics of the new *Gazania*. The photographs were taken of a plant 9 months in age of 'DwGzHy01' as grown in a greenhouse in a 21-cm container in in Waddxinveen, The Netherlands.

The photograph in FIG. 1 provides a top view of a plant of 'DwGzHy01' in bloom.

Figure 1:
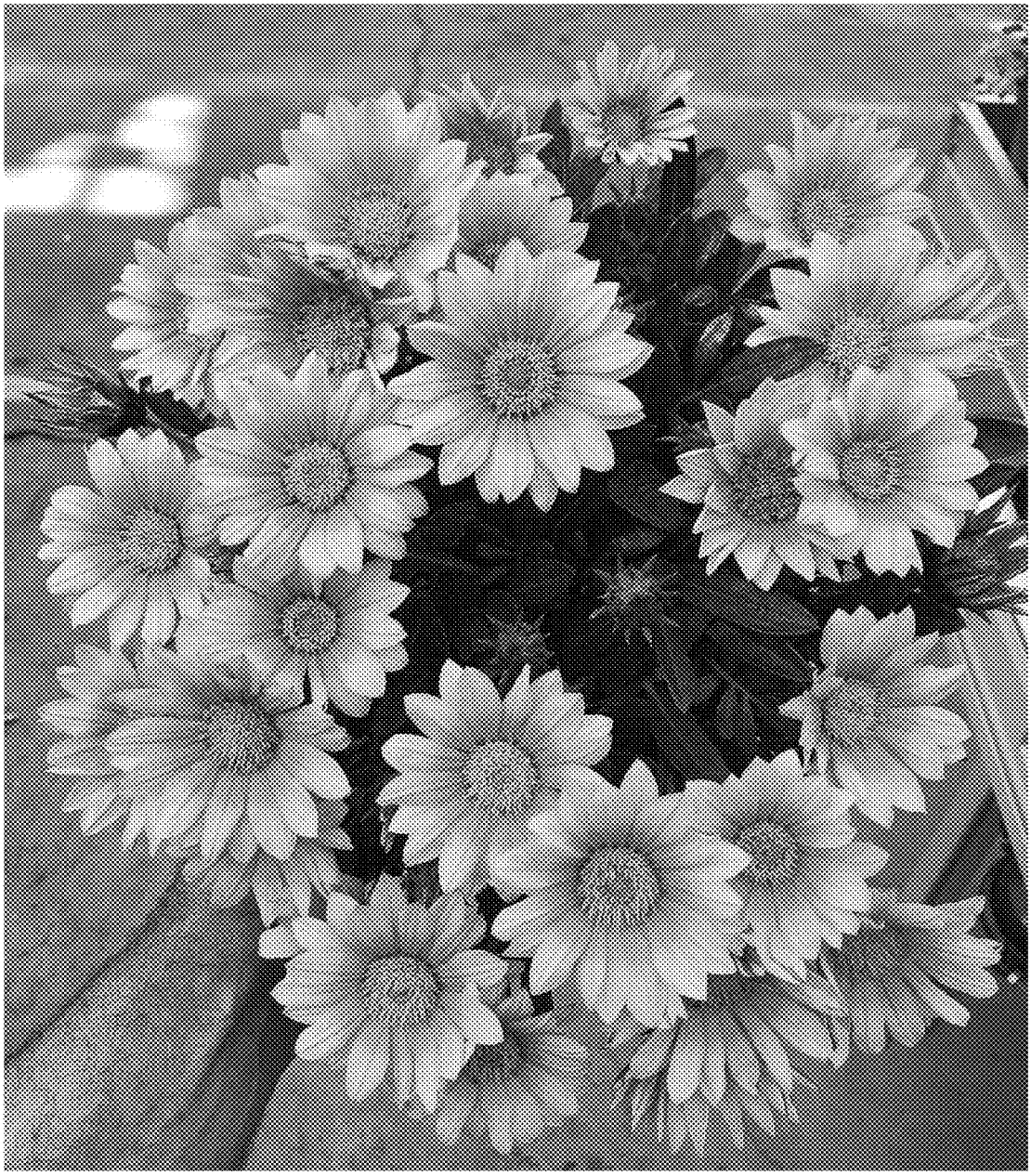
Figure 2:
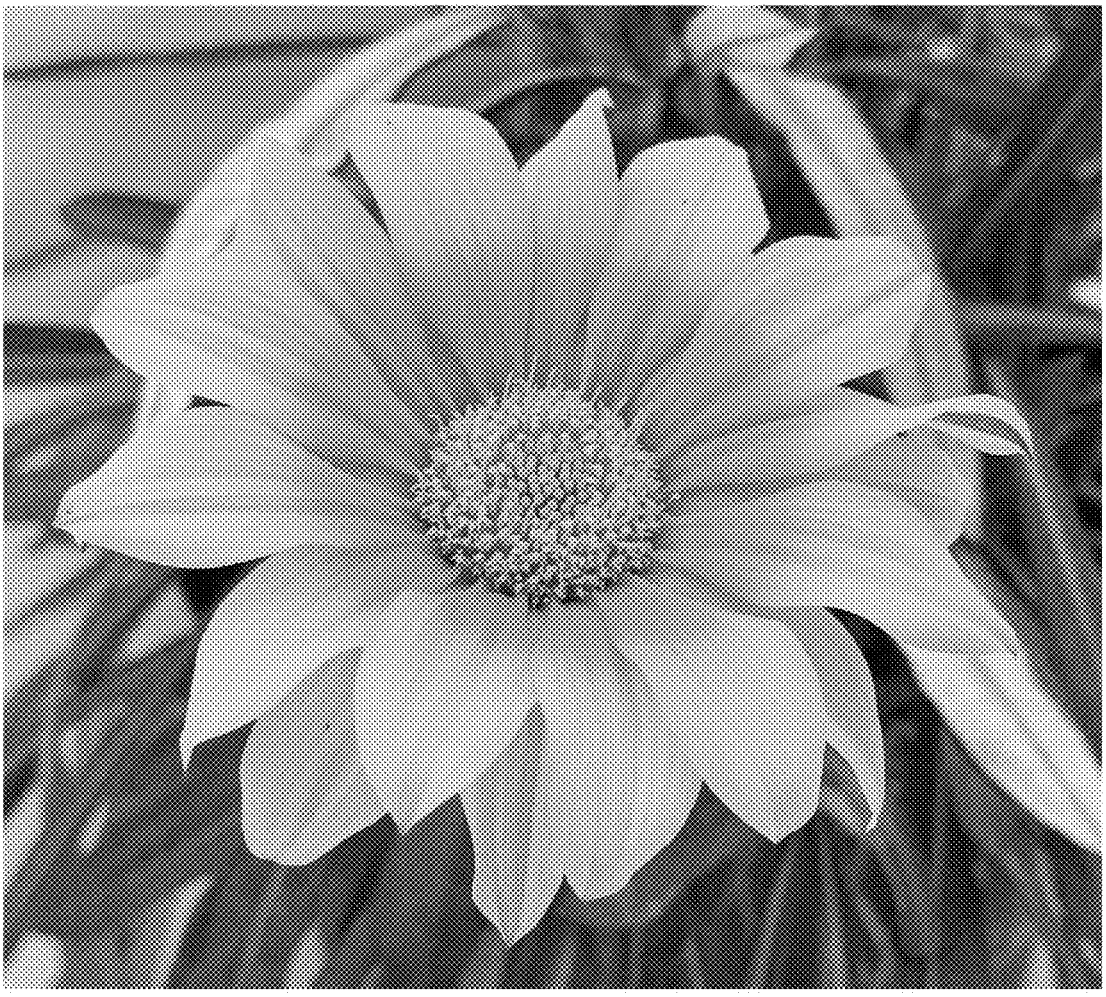

The photograph in FIG. 2 provides a close-up view of an inflorescence of 'DwGzHy01'.

Figure 3:
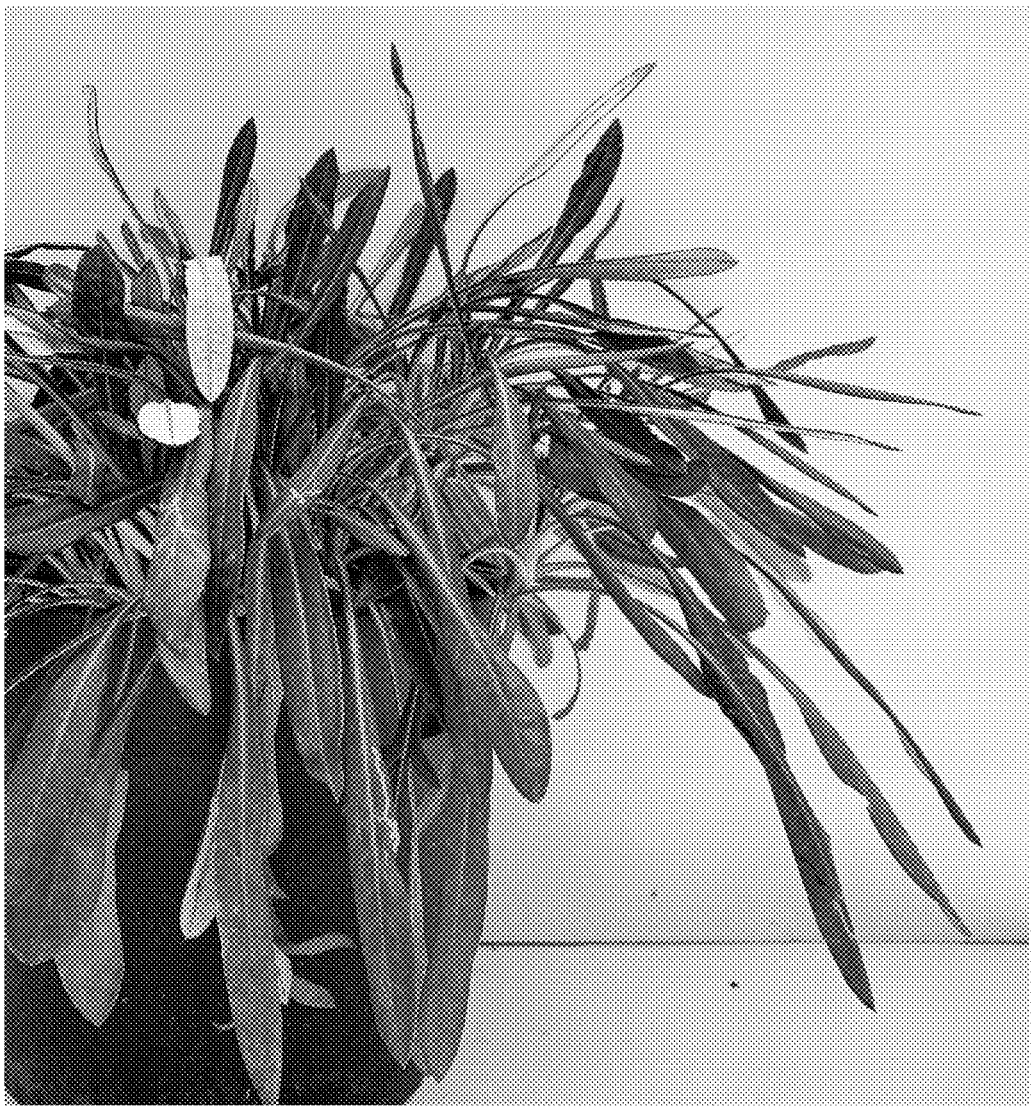

The photograph in FIG. 3 provides a close-up view of the foliage of 'DwGzHy01'.

The colors in the photographs are as close as possible with the photographic and printing technology utilized and color values cited in the detailed botanical description accurately describe the colors of the new *Gazania*.

DETAILED BOTANICAL DESCRIPTION

The following is a detailed description of 9-month-old plants of 'DwGzHy01' as grown indoors in 21-cm containers in Waddxinveen, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

- *Blooming period*.—May through October in The Netherlands and longer in South Africa.
- *Plant type*.—Herbaceous perennial.
- *Plant habit*.—Compact, bushy, low growing, non-spreading, upright leafy flowering stems with inflorescences held above the foliage.
- *Height and spread*.—Reaches an average of 16 cm in height and 46 cm in width as a 9-month old plant in a container.
- *Hardiness*.—At least to U.S.D.A Zones 9 to 11.
- *Diseases and pests*.—Good resistance has been observed to *Fusarium* spp.
- *Environmental stresses*.—Heat and drought tolerance.
- *Root description*.—Fine.
- *Propagation*.—Tissue culture and stem cuttings.
- *Time required for root initiation*.—An average of 4 to 6 weeks for root initiation, 10 to 12 weeks to produce a young plant in a P15 container from a rooted plug.
- *Growth rate*.—Vigorous.

Stem description:

- *Shape*.—Rounded.
- *Stem color*.—145A.
- *Stem strength*.—Strong.
- *Stem size*.—An average of 6 cm in length and 3.5 mm in width.
- *Stem surface*.—Glabrous.
- *Internode length*.—Up to 1 cm.

Foliage description:

- *Leaf division*.—Simple.
- *Leaf margins*.—Serrulate.
- *Leaf size*.—Entire leaves; an average of 15 cm in length and 1.5 cm in width, lobed leaves; 15 cm in length, 4.5 cm in width.
- *Leaf shape*.—Simple oblanceolate to pinnately seven lobed.
- *Leaf base*.—Attenuate.
- *Leaf apex*.—Acute.
- *Leaf venation*.—Pinnate, upper surface 137C, lower surface 139C.
- *Leaf attachment*.—Sessile.
- *Leaf arrangement*.—Alternate.
- *Leaf surface*.—Upper surface glabrous and glossy, lower surface pubescent.
- *Leaf color*.—Upper surface 137A, lower surface 190D.

Flower description:

- *Inflorescence type*.—Composite with a single row of ray florets surrounding disc florets in the center, forming a radiant head, inflorescences are borne on stem terminals.
- *Lastingness of inflorescence*.—8 to 10 days, self-cleaning.
- *Fragrance*.—None.
- *Quantity of inflorescences*.—Free flowering, an average of 2 per lateral branch.
- *Inflorescence size*.—Average of 7.2 cm in diameter, 2.8 cm in height, disc 1.9 cm in diameter.
- *Inflorescence buds*.—Ovoid in shape, an average of 1.5 cm in diameter, 1.7 cm in length, 137A in color.
- *Peduncle*.—Rounded in shape, strong, an average of 14 cm in length and 3 mm in diameter, 145A in color, surface very slightly pubescent.

Phyllaries (involucral bracts):

- *Phyllary number*.—18 in 2 rows; outer (lower) row 9, inner (upper) row 9.
- *Phyllary size*.—Average of 1.2 cm in length, 1.5 mm in width.
- *Phyllary color*.—Upper and lower surface between 144A and 144B.
- *Phyllary texture*.—Both surfaces matte and very slight pubescent.
- *Phyllary apex*.—Acute.

*Phyllary base*.—Truncate and fused.

*Phyllary shape*.—Linear-lanceolate.

Ray florets (sterile):

*Number*.—20 (arranged in 2 rows).

*Shape*.—Oblanceolate to obovate.

*Size*.—An average of 3 cm in length and 1.8 cm in width.

*Apex*.—Broadly acute.

*Base*.—Attenuate.

*Margins*.—Entire.

*Aspect*.—Held mainly horizontal and slightly upwards, perpendicular to peduncle.

*Texture*.—Both surfaces smooth.

*Color*.—Upper surface when opening and fully open; top to mid-section 14A, base 28B, lower surface when opening and fully open; 13B, margins 14A, stripe in the center N170A, base a hint of 145A.

Disc florets (female):

*Number*.—An average of 180.

*Shape*.—Tubular, corolla is fused, flared and slightly curled at apex.

*Size*.—8 mm in length, 1.5 mm in width.

*Color*.—En masse; 14A, individual; base N155D, center 13B, top 14A.

*Receptacle*.—An average of 2 cm in diameter and 1 cm in depth, 144A in color.

Reproductive organs:

*Presence*.—Disc flowers only.

*Gynoecium*.—1 Pistil; an average of 1.2 cm in length, style; very fine, 1.1 cm in length, 12A in color, stigma; 12A in color, bifid, ovary is inferior, oblong in shape, an average of 3 mm in length and 1 mm in width, and 145C in color.

*Androecium*.—None observed.

*Seed*.—Not produced.

It is claimed:

1. A new and distinct cultivar of *Gazania* plant named 'DwGzHy01' as herein illustrated and described.

* * * * *